United States Patent
Shimamoto et al.

(10) Patent No.: US 11,484,192 B2
(45) Date of Patent: Nov. 1, 2022

(54) OPTICAL-SCANNING-TYPE OBSERVATION PROBE AND OPTICAL-SCANNING-TYPE OBSERVATION DEVICE

(71) Applicant: OLYMPUS CORPORATION, Tokyo (JP)

(72) Inventors: Atsuyoshi Shimamoto, Tokyo (JP);
Keiichiro Nakajima, Tokyo (JP);
Masashi Yamada, Tokyo (JP);
Takamitsu Sakamoto, Tokyo (JP);
Mitsuru Namiki, Saitama (JP);
Mikihiko Terashima, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 774 days.

(21) Appl. No.: 16/516,485

(22) Filed: Jul. 19, 2019

(65) Prior Publication Data
US 2019/0335986 A1 Nov. 7, 2019

Related U.S. Application Data

(63) Continuation of application No. PCT/JP2018/002222, filed on Jan. 25, 2018.

(30) Foreign Application Priority Data

Jan. 27, 2017 (JP) .............................. JP2017-012738

(51) Int. Cl.
*A61B 1/07* (2006.01)
*A61B 1/00* (2006.01)
*G02B 3/00* (2006.01)

(52) U.S. Cl.
CPC ............ *A61B 1/07* (2013.01); *A61B 1/00096* (2013.01); *A61B 1/00172* (2013.01); *G02B 3/0087* (2013.01)

(58) Field of Classification Search
CPC ... A61B 1/07; A61B 1/00096; A61B 1/00172; G02B 3/0087; G02B 23/2446; G02B 23/26; G02B 26/103
See application file for complete search history.

(56) References Cited

U.S. PATENT DOCUMENTS

| 6,845,190 B1 | 1/2005 | Smithwick et al. |
| 2001/0055462 A1 | 12/2001 | Seibel |

(Continued)

FOREIGN PATENT DOCUMENTS

| JP | 2011-43793 A | 3/2011 |
| JP | 5025877 B2 | 9/2012 |

(Continued)

OTHER PUBLICATIONS

International Search Report dated Feb. 27, 2018 issued in PCT/JP2018/002222.

*Primary Examiner* — Fernando Alcon
(74) *Attorney, Agent, or Firm* — Scully, Scott, Murphy & Presser, P.C.

(57) ABSTRACT

An optical-scanning-type observation probe is provided with: an imaging optical system that illumination light scanned by an optical scanner enters and that focuses the illumination light in the form of a spot, multiple times; a projection optical system that emits illumination light coming from a focus position focused by the imaging optical system, toward a subject in the form of a spot; and a light-receiver that is provided independently of the imaging optical system and the projection optical system and that receives reflected light of the illumination light, the reflected light coming from the subject, via a light path different from that of the imaging optical system and the projection optical system.

14 Claims, 14 Drawing Sheets

(56) References Cited

U.S. PATENT DOCUMENTS

| | | |
|---|---|---|
| 2002/0064341 A1 | 5/2002 | Fauver et al. |
| 2004/0122328 A1 | 6/2004 | Wang et al. |
| 2004/0254474 A1 | 12/2004 | Seibel et al. |
| 2006/0170930 A1 | 8/2006 | Li |
| 2007/0213618 A1* | 9/2007 | Li .................... A61B 1/00172 |
| | | 600/476 |
| 2007/0280614 A1* | 12/2007 | Karasawa ............. G02B 26/10 |
| | | 348/45 |
| 2008/0221388 A1 | 9/2008 | Seibel et al. |
| 2009/0235396 A1 | 9/2009 | Wang et al. |
| 2011/0019255 A1 | 1/2011 | Murayama |
| 2013/0060087 A1* | 3/2013 | Yoshida .................. A61B 1/07 |
| | | 600/112 |
| 2015/0238071 A1 | 8/2015 | Hua et al. |
| 2016/0231561 A1* | 8/2016 | Kasai .................... G02B 23/26 |
| 2018/0110402 A1* | 4/2018 | Yamada ............ A61B 1/00193 |
| 2018/0116492 A1* | 5/2018 | Yamada .............. H04N 5/2354 |
| 2019/0219831 A1* | 7/2019 | Duckett ............ A61B 1/00009 |
| 2019/0227303 A1* | 7/2019 | Fujiwara ................ G02B 26/10 |
| 2022/0110724 A1* | 4/2022 | Moalem .................. A61B 1/24 |

FOREIGN PATENT DOCUMENTS

| | | |
|---|---|---|
| JP | 2014-18555 A | 2/2014 |
| WO | WO 2001/97902 A2 | 12/2001 |
| WO | WO 2014/017064 A1 | 1/2014 |

* cited by examiner

OPTICAL-SCANNING-TYPE OBSERVATION PROBE AND OPTICAL-SCANNING-TYPE OBSERVATION DEVICE

CROSS-REFERENCE TO RELATED APPLICATIONS

This is a continuation of International Application PCT/JP2018/002222, with an international filing date of Jan. 25, 2018, which is hereby incorporated by reference herein in its entirety.

TECHNICAL FIELD

The present invention relates to an optical-scanning-type observation probe and an optical-scanning-type observation device.

BACKGROUND ART

There is a known scanning endoscope provided with an optical fiber scanner that scans illumination light emitted from an optical fiber by vibrating the optical fiber (for example, see Publication of Japanese Patent No. 5025877). Publication of Japanese Patent No. 5025877 proposes application of an optical fiber scanner to a rigid endoscope that relays signal light, such as reflected light from a subject, from an objective lens to an image acquisition element by using a relay lens.

SUMMARY OF INVENTION

According to a first aspect, the present invention provides an optical-scanning-type observation probe including: an imaging optical system that illumination light scanned by an optical scanner enters and that focuses the illumination light in the form of a spot, multiple times; a projection optical system that emits the illumination light coming from a focus position focused by the imaging optical system, toward a subject in the form of a spot; and a light-receiver that is provided independently of the imaging optical system and the projection optical system and that receives signal light produced in the subject through irradiation of the illumination light, via a light path different from that of the imaging optical system and the projection optical system.

The above-described first aspect may further include a correction optical system that corrects inclination of a chief ray of the illumination light scanned by the optical scanner and entering the imaging optical system, with respect to the optical axis of the imaging optical system, so as to bring the chief ray close to parallel to the optical axis.

In the above-described first aspect, the imaging optical system may be provided with a gradient index lens whose end face, from which the illumination light scanned by the optical scanner enters, is a convex face; and the correction optical system may be formed of the convex face of the gradient index lens.

In the above-described first aspect, the imaging optical system may be constituted by: a first imaging optical system that the illumination light scanned by the optical scanner enters, that corrects inclination of the chief ray of the illumination light so as to bring the chief ray close to parallel to the optical axis, and that emits the illumination light for which inclination of the chief ray has been corrected; and a second imaging optical system that is disposed on an emission side of the first imaging optical system; and the correction optical system may be formed of the first imaging optical system.

In the above-described first aspect, the imaging optical system may be constituted by a first imaging optical system and a second imaging optical system that is disposed on an emission side of the first imaging optical system; and the first imaging optical system may correct aberration that occurs in at least one of the projection optical system and the second imaging optical system.

In the above-described first aspect, the imaging optical system may be constituted by a first imaging optical system and a second imaging optical system that is disposed on an emission side of the first imaging optical system; and the second imaging optical system may have a lens diameter approximately equivalent to a lens diameter of the projection optical system and may be integrated with the projection optical system.

The above-described first aspect may further include an aperture stop that is disposed in the vicinity of a pupil position of one of the imaging optical system and the projection optical system.

In the above-described first aspect, at least an emission-side part of the imaging optical system and the projection optical system may be each formed of a gradient index lens; and an emission-side end face of the gradient index lens that forms the imaging optical system and an incident-side end face of the gradient index lens that forms the projection optical system may be combined with each other.

In the above-described first aspect, the combined faces of the gradient index lenses may be disposed at a position different from a focus position of the illumination light focused by the imaging optical system.

In the above-described first aspect, the imaging optical system may be constituted by a first imaging optical system and a second imaging optical system that is disposed on an emission side of the first imaging optical system; and a lens surface of the second imaging optical system may be disposed at a position different from a focus position of the illumination light focused by the first imaging optical system.

According to a second aspect, the present invention provides an optical-scanning-type observation device including: a light source that produces illumination light; an optical scanner that scans the illumination light emitted from the light source; and any one of the above-described optical-scanning-type observation probes.

In the above-described second aspect, the optical scanner may be provided with an optical fiber that guides the illumination light emitted from the light source and that emits the illumination light from a distal end thereof, and may vibrate the optical fiber in radial directions of the optical fiber so as to satisfy the following expression (1):
h≤π×d×D×NA'/4λ (1),
where h is a half amplitude of a distal end of the optical fiber; d is a mode field diameter of the optical fiber; D is an entrance pupil diameter of the imaging optical system; NA' is a numerical aperture on an incident side of the imaging optical system; and λ is a wavelength of the illumination light.

In the above-described second aspect, the optical scanner may be provided with a galvanometer mirror that scans the illumination light emitted from the light source, and may swing the galvanometer mirror so as to satisfy the following expression (2): tan(2α)≤D×NA'/w (2),
where α is half of the total swing angle of the galvanometer mirror; w is a luminous flux diameter of the illumination light incident on the galvanometer mirror; NA' is a numerical aperture on an incident side of the imaging optical system; and D is an entrance pupil diameter of the imaging optical system.

In the above-described second aspect, the optical scanner may have an emission end from which the illumination light is emitted toward the imaging optical system; and the optical-scanning-type observation device may further include an adjustment mechanism that adjusts relative positions of the emission end of the optical scanner and the imaging optical system, in a direction parallel to the optical axis of the imaging optical system and in a direction perpendicular to the optical axis thereof.

DESCRIPTION OF EMBODIMENTS

An optical-scanning-type observation probe 1 and an optical-scanning-type observation device 100 provided with the same according to a first embodiment of the present invention will be described below with reference to FIGS. 1 to 6.

Figure 1:
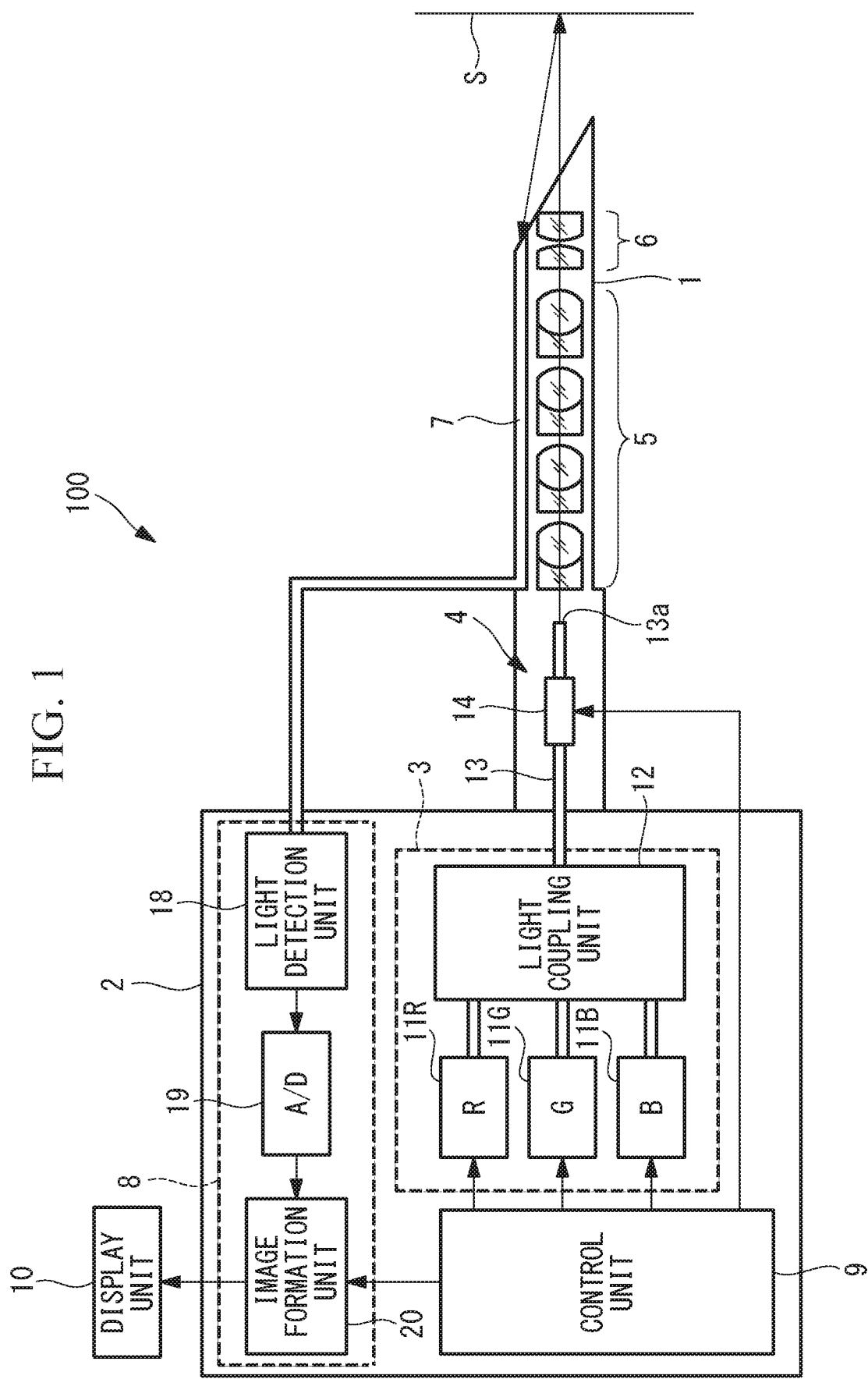
FIG. 1 is a view showing the overall configuration of an optical-scanning-type observation device according to a first embodiment of the present invention.

As shown in FIG. 1, the optical-scanning-type observation device 100 of this embodiment is a rigid endoscope device that is provided with: an insertion portion 1 that is rigid and has a straight shape and that is inserted into a body; and a housing 2 that is connected to a base end of the insertion portion 1. The optical-scanning-type observation probe of this embodiment is formed of the insertion portion 1.

The optical-scanning-type observation device 100 is provided with: a light source 3; an optical scanner 4 that scans illumination light supplied from the light source 3; an imaging optical system 5 and a projection optical system 6 that guide the illumination light emitted from the optical scanner 4, while focusing the illumination light multiple times, and that emit the illumination light toward a subject S; a light-receiver 7 that receives reflected light (signal light) from the subject S; an image acquisition unit 8 that acquires an image based on the reflected light received by the light-receiver 7; and a controller 9 that controls the light source 3, the optical scanner 4, and the image acquisition unit 8.

The light source 3, the optical scanner 4, the image acquisition unit 8, and the controller 9 are provided in the housing 2, and the imaging optical system 5, the projection optical system 6, and the light-receiver 7 are provided in the insertion portion 1. A display 10 that displays an image acquired by the image acquisition unit 8 is connected to the housing 2.

The light source 3 is provided with: three laser light sources (light sources) 11R, 11G, and 11B, such as laser diodes, that generate red light, green light, and blue light, respectively; and a light coupling unit 12 that combines light of three colors from the laser light sources 11R, 11G, and 11B and that guides the combined light to an optical fiber 13 of the optical scanner 4. The light coupling unit 12 is formed of a fiber-type combiner, a dichroic prism, or the like.

Figure 2:
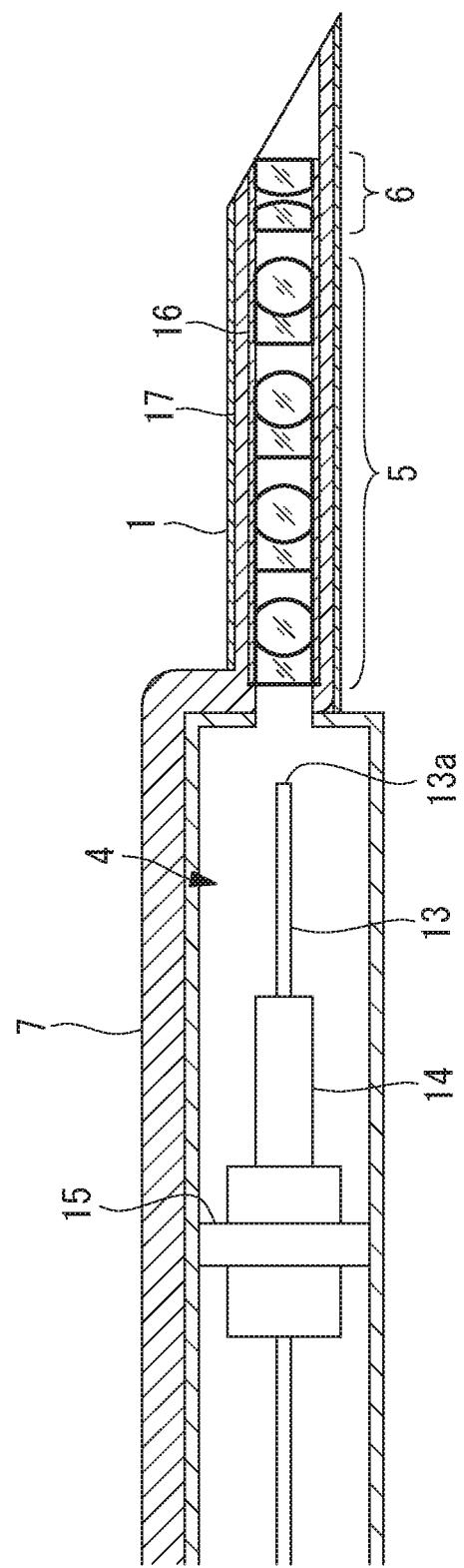
FIG. 2 is a view showing the configuration of an insertion portion and an optical scanner of the optical-scanning-type observation device shown in FIG. 1.

As shown in FIG. 2, the optical scanner 4 is provided with: the optical fiber 13, which is formed of a single-mode fiber; and an actuator 14 that is provided at a distal end section of the optical fiber 13 and that vibrates a distal end (emission end) 13a of the optical fiber 13. Reference sign 15 denotes a fixing part that fixes an intermediate position of the optical fiber 13 in the longitudinal direction to a housing accommodating the optical fiber 13, such that the distal end section of the optical fiber 13 is supported in a cantilever manner. The actuator 14 is, for example, a piezoelectric actuator that is provided with a piezoelectric element disposed on an outer circumference of the optical fiber 13, and two-dimensionally vibrates the emission end 13a of the optical fiber 13 in radial directions of the optical fiber 13 when a voltage is applied from the controller 9.

The insertion portion 1 has an inner cylinder 16 and an outer cylinder 17 that are made of a rigid material, such as metal, and that are coaxially disposed. The imaging optical system 5 and the projection optical system 6 are provided in the inner cylinder 16, which is located at an inner side, the projection optical system 6 is disposed at a distal end section of the insertion portion 1, and the imaging optical system 5 is disposed between the optical fiber 13 and the projection optical system 6.

The imaging optical system 5 guides illumination light entering from the emission end 13a of the optical fiber 13, to the projection optical system 6 while focusing the illumination light multiple times on a plurality of focus positions arranged on the optical axis.

The projection optical system 6 focuses the illumination light coming from the focus position (final focus position)

on which the imaging optical system 5 finally focuses the illumination light, so as to cause the illumination light to form a spot on the subject S, and emits the illumination light at a wide angle, thus projecting the illumination light onto the subject S. Although it is preferred that the projection magnification of the projection optical system 6 be greater than 1 so as to enlarge the spot of the illumination light, the projection magnification may also be equal to or less than 1.

Figure 3:
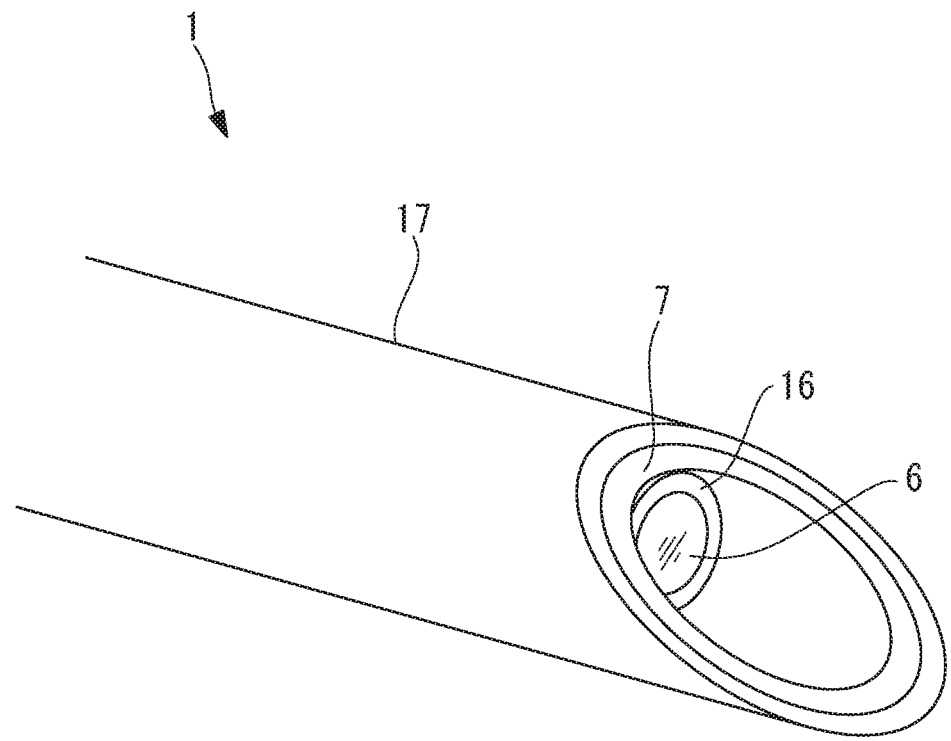
FIG. 3 is a perspective view showing a distal end section of the insertion portion shown in FIG. 2.

The light-receiver 7 is, for example, a cylindrical optical fiber bundle, is disposed in a cylindrical interspace formed between an outer circumferential surface of the inner cylinder 16 and an inner circumferential surface of the outer cylinder 17, and is bonded to the inner circumferential surface of the outer cylinder 17. As shown in FIG. 3, for example, distal-end faces of the outer cylinder 17 and the light-receiver 7 may be blade faces formed so as to be diagonal to the longitudinal direction. Accordingly, the insertion portion 1 can be easily inserted into a living body, like a puncture needle. The shapes of the distal-end faces of the outer cylinder 17 and the light-receiver 7 are not limited thereto and can be appropriately modified.

Figure 4:
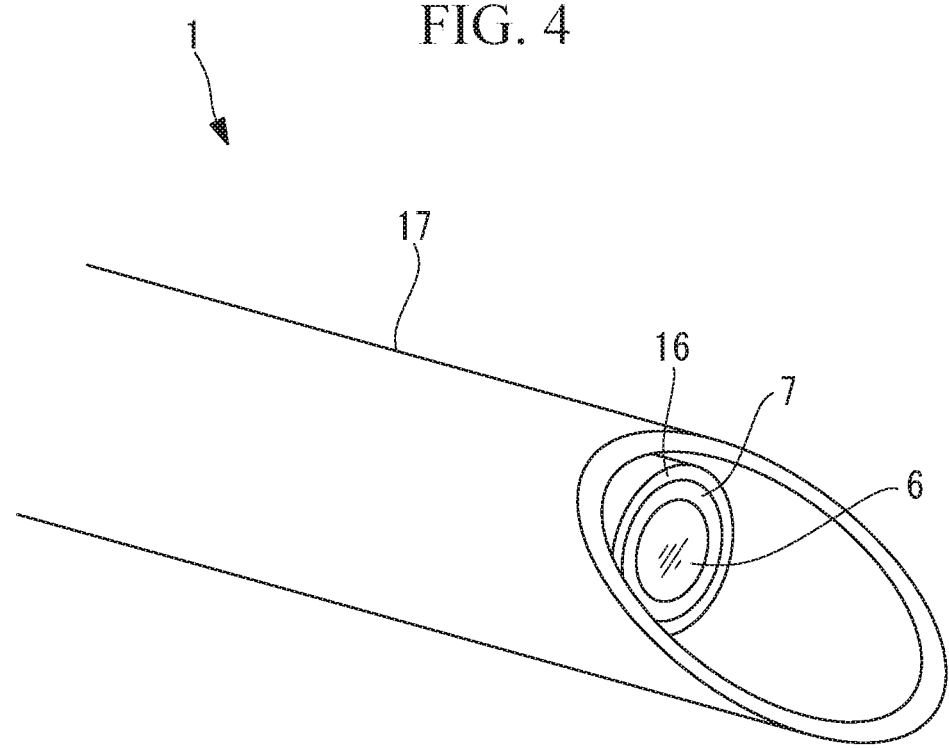
FIG. 4 is a perspective view showing a modification of the insertion portion shown in FIG. 2.

As another form, as shown in FIG. 4, the light-receiver 7 may be formed of an optical fiber bundle that is disposed in a cylindrical interspace formed between an inner circumferential surface of the inner cylinder 16 and an outer circumferential surface of the projection optical system 6 and that is bonded thereto. The outer cylinder 17 may have a blade face formed so as to be diagonal to the longitudinal direction, for example, as shown in FIG. 3. Accordingly, the insertion portion 1 can be easily inserted into a living body, like a puncture needle. The shape of the distal-end face of the outer cylinder 17 is not limited thereto and can be appropriately modified.

The outer side surfaces of lenses that constitute the imaging optical system 5 and the projection optical system 6 are painted with a paint (for example, black paint) that absorbs illumination light. Reflection of illumination light at the side surfaces of the lenses is prevented by the paint, thereby suppressing the occurrence of flare light etc. In a case in which the outer side surfaces of the lenses and the inner circumferential surface of the inner cylinder 16 are in close contact with each other, the paint may be painted on the inner circumferential surface of the inner cylinder 16, instead of the outer side surfaces of the lenses.

The image acquisition unit 8 is provided with: a light detector 18 that photo-electrically converts reflected light received from the light-receiver 7; an A/D converter 19 that converts an analog signal output from the light detector 18 to a digital signal; and an image formation unit 20 that forms an image on the basis of the output from the A/D converter 19.

The controller 9 controls lighting timing of the three laser light sources 11R, 11G, and 11B and also controls scan positions of illumination light, from the respective laser light sources 11R, 11G, and 11B, scanned by the optical scanner 4. Furthermore, the controller 9 sends scan-position information on illumination light to be emitted from the insertion portion 1, to the image formation unit 20.

The image formation unit 20 forms an image on the basis of: the digital signal output from the A/D converter 19, i.e., intensity information on reflected light; and the scan-position information on illumination light, sent from the controller 9. The image formed by the image formation unit 20 is sent to the display 10 and is displayed on the display 10.

The operation of the thus-configured optical-scanning-type observation device 100 of this embodiment will be described below.

In order to observe the inside of the body of a patient by using the optical-scanning-type observation device 100 of this embodiment, the insertion portion 1 is inserted into the body. At this time, the controller 9 actuates the three laser light sources 11R, 11G, and 11B to sequentially emit three types of illumination light in a predetermined light-emission order (for example, in the order of R, G, and B) and controls the actuator 14, by a command signal from the controller 9, to sequentially change the scan position of the illumination light. For example, the emission end 13a of the optical fiber 13 is moved in a spiral manner through actuation of the actuator 14, thereby radiating the illumination light so as to array spots of the illumination light on a spiral trajectory on the subject S. Note that the movement pattern of the emission end 13a of the optical fiber 13 and the scan pattern of the spot of illumination light may be other patterns, such as a lissajous pattern or a raster pattern, instead of the spiral pattern. Note that, although a description will be given here of a case in which three types of light, i.e., red light, green light, and blue light, are used as illumination light, the number of types of illumination light may be one or more.

When illumination light is emitted from the laser light sources 11R, 11G, and 11B, reflected light at each scan position on the subject S in the body enters the light-receiver 7 at the distal-end face of the insertion portion 1, is guided by the light-receiver 7 to the light detector 18, and is detected therein. Intensity information on the detected reflected light is converted into a digital signal by the A/D converter 19 and is then sent to the image formation unit 20. Because the controller 9 has sent, to the image formation unit 20, information on the scan position of the spot of the illumination light on the subject S, the scan-position information being associated with the intensity information on the reflected light, the image formation unit 20 arrays the intensity information on the detected reflected light in association with the scan position, thereby making it possible to generate a two-dimensional color image.

In this case, according to the optical-scanning-type observation device 100 of this embodiment, the light-receiver 7, which is independent of the optical systems 5 and 6 forming a light path of illumination light, is provided, and reflected light is guided by the light-receiving unit 7 to the light detector 18 without passing through the light path of illumination light. Therefore, reflected light of illumination light that is produced in the optical systems 5 and 6 is not mixed into reflected light that is received by the light-receiver 7, and reflected light from the subject S is detected with a high signal-to-noise ratio. Accordingly, there is an advantage in that a clear image of the subject S can be acquired.

The optical scanner 4 is disposed closer to the base end than the insertion portion 1 is, and only the optical systems 5 and 6 and the light-receiver 7 are provided inside the cylinders 16 and 17 of the insertion portion 1. In this way, because the insertion portion 1 has a simple configuration, there is an advantage in that the insertion portion 1 can be reduced in diameter so as to be suitable for, for example, puncture and insertion into the body.

When optical systems having the same effective diameter are used, the optical-scanning-type observation device 100, which acquires an image by continuously scanning spot-shaped illumination light, can obtain higher resolution, compared with a conventional rigid endoscope device that forms an image of reflected light from the subject S and that acquires the image by a two-dimensional imaging device.

Therefore, there is an advantage in that a high-resolution image can be acquired even with the insertion portion 1, which has a small diameter.

Figure 5:
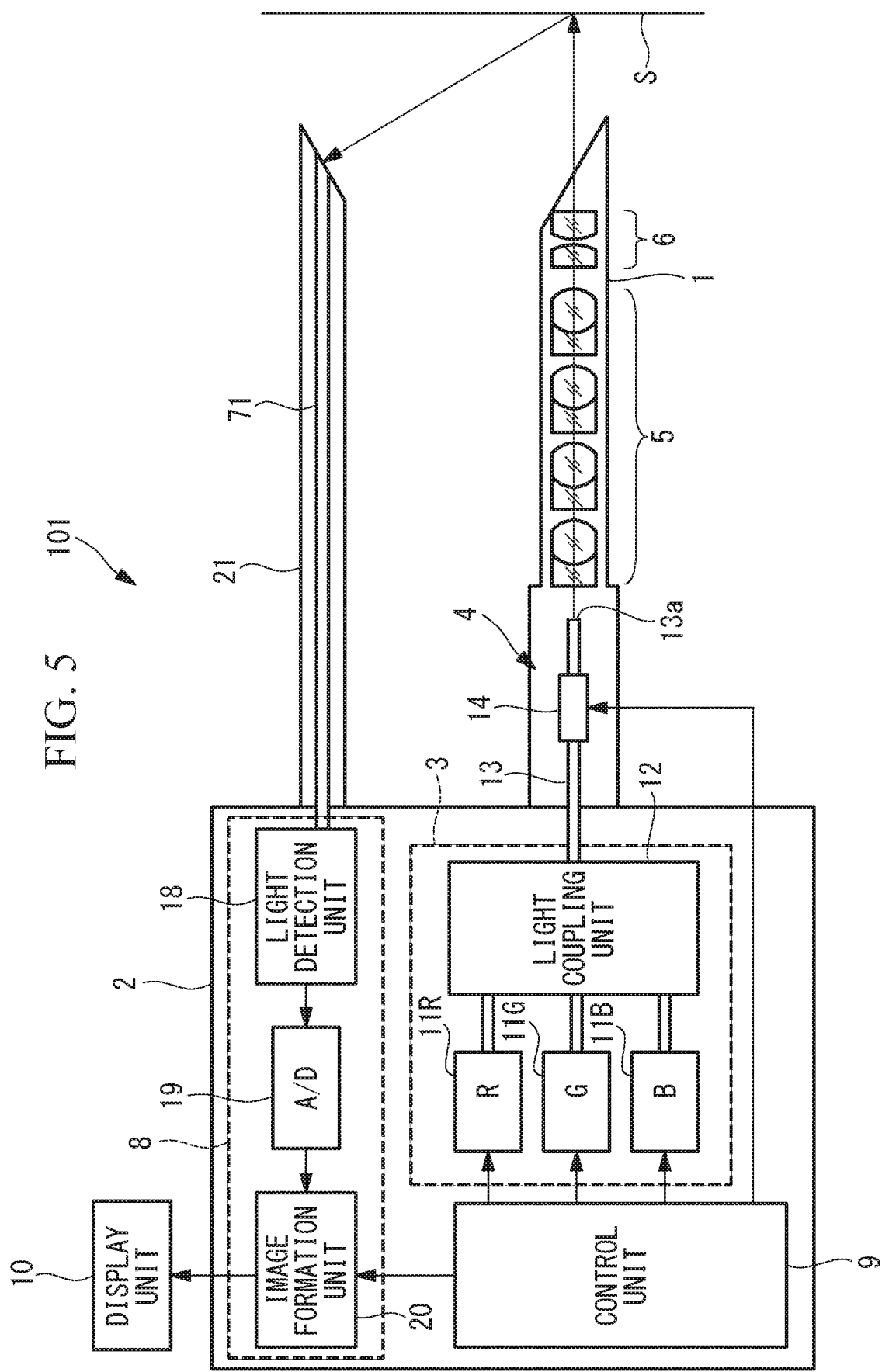
FIG. 5 is a view showing the overall configuration of a modification of the optical-scanning-type observation device shown in FIG. 1.
Figure 6:
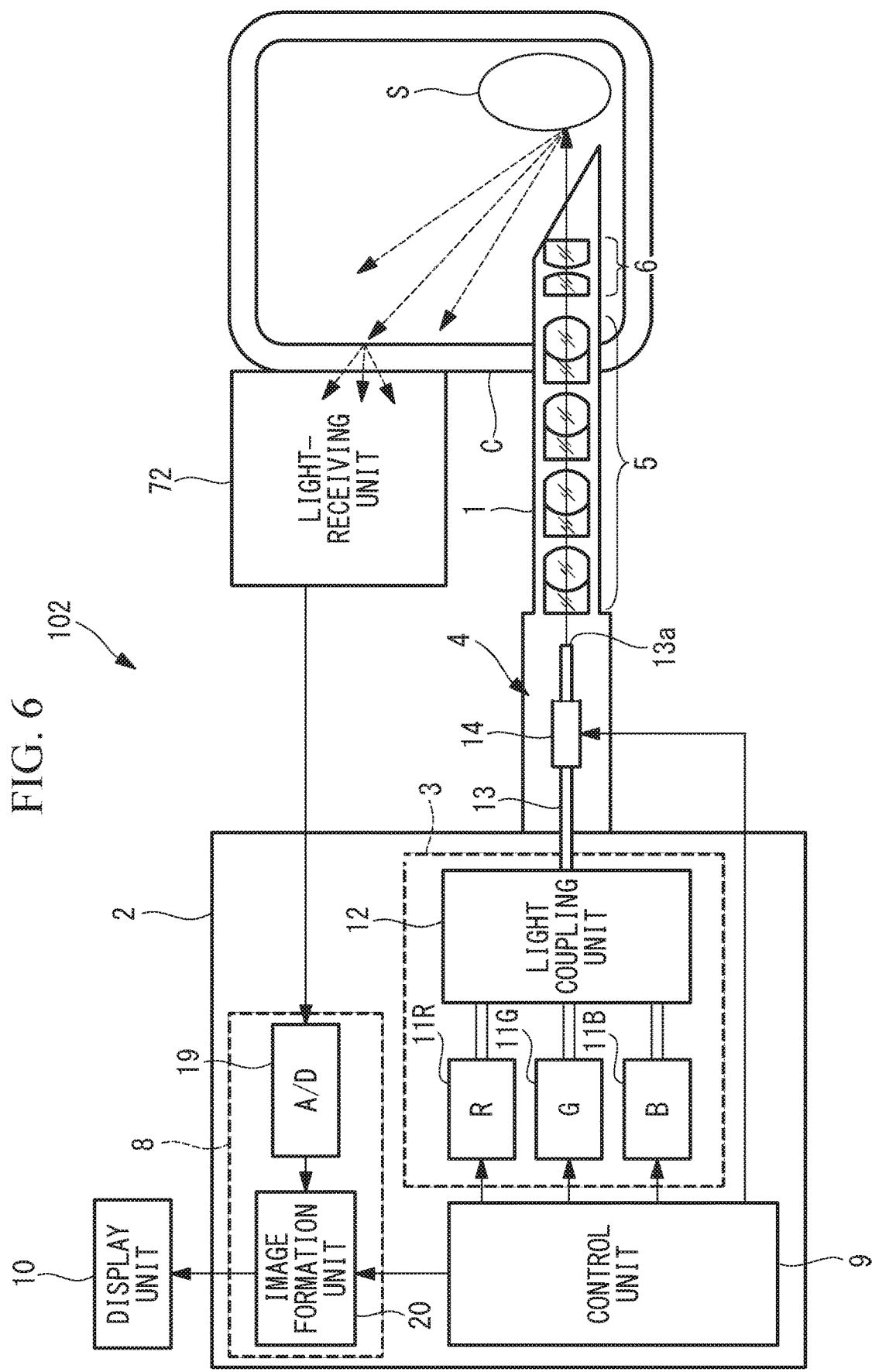
FIG. 6 is a view showing the overall configuration of another modification of the optical-scanning-type observation device shown in FIG. 1.

In this embodiment, although the light-receiver 7 is provided integrally with the imaging optical system 5 and the projection optical system 6, instead of this, as shown in FIGS. 5 and 6, it is also possible to adopt a light-receiver 71 or 72 that is separate from the imaging optical system 5 and the projection optical system 6.

An optical-scanning-type observation probe in an optical-scanning-type observation device 101 shown in FIG. 5 is provided with another insertion portion 21 that has a puncture-needle shape having a blade face, as in the insertion portion 1, and the insertion portion 21 is provided therein with an optical fiber bundle that forms the light-receiver 71. The insertion portion 1 for illumination and the insertion portion 21 for light reception are separately inserted into the body.

Figure 7:
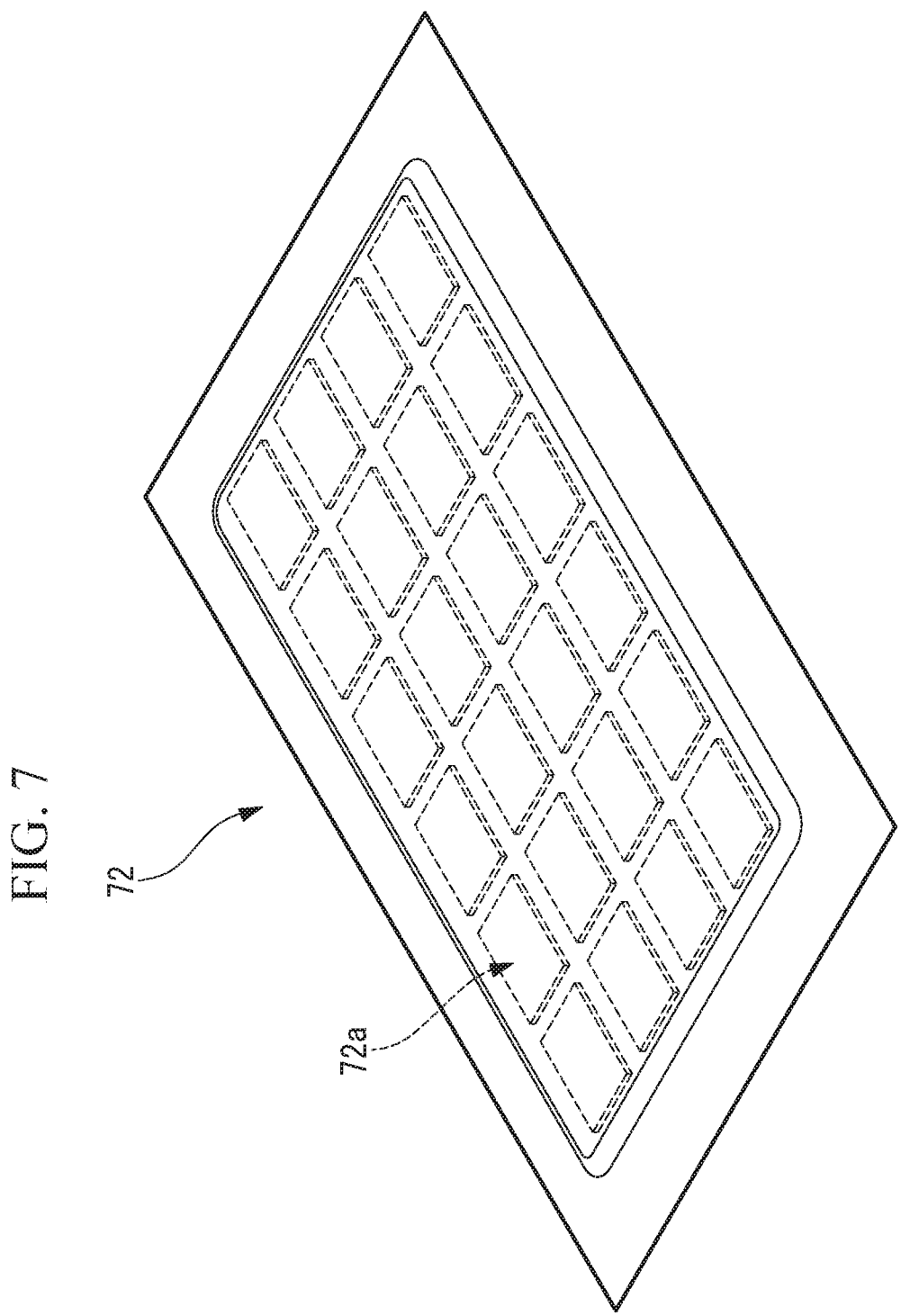
FIG. 7 is a view showing a light-receiver in an optical-scanning-type observation device shown in FIG. 6.

An optical-scanning-type observation probe in an optical-scanning-type observation device 102 shown in FIG. 6 is provided with the light-receiver 72, which is disposed on a body surface C of a patient in a contact state. As shown in FIG. 7, the light-receiver 72 is, for example, an adhesive sheet on which a plurality of photodetectors 72a, such as avalanche photodiodes, are arrayed in an array. Each of the photodetectors 72a has sensitivity to all wavelength bands of illumination light emitted from the light source 3. During observation, the light-receiver 72, which is formed of the adhesive sheet, is adhered to the body surface of the patient, and reflected light at respective scan positions on the subject S in the body transmits through body tissues, enters the photodetectors 72a of the light-receiver 72, and is detected therein. In this way, by adopting the light-receiver 72, which is used outside the body, the insertion portion 1 can be further reduced in diameter.

Next, an optical-scanning-type observation device according to a second embodiment of the present invention will be described with reference to FIGS. 8 to 10.

In this embodiment, configurations that are different from those in the first embodiment are mainly described, the same reference signs are assigned to configurations that are common to those in the first embodiment, and a description thereof will be omitted.

The optical-scanning-type observation device of this embodiment is provided with the light source 3, the optical scanner 4, an imaging optical system 51, a projection optical system 61, the light-receiver 7, the image acquisition unit 8, and the controller 9.

Figure 8:
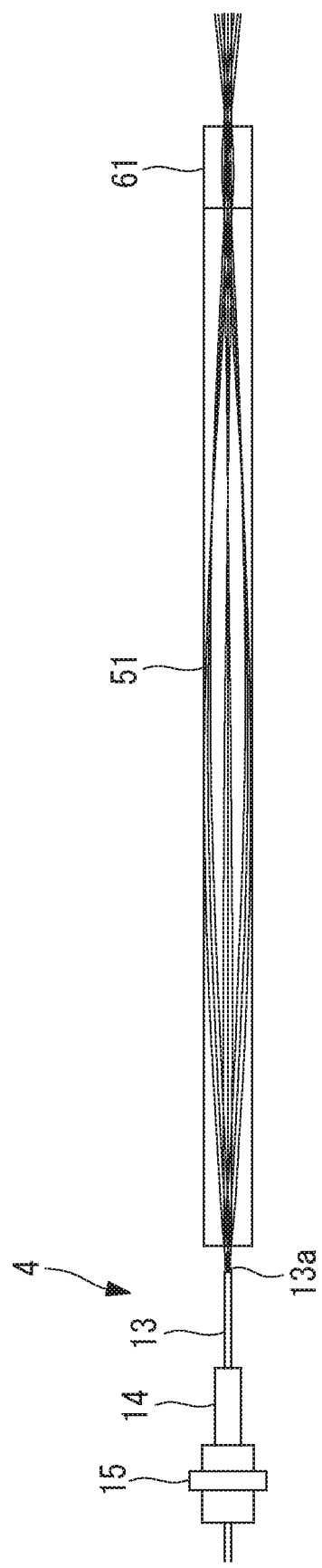
FIG. 8 is a view showing the configuration of an optical scanner, an imaging optical system, and a projection optical system in an optical-scanning-type observation device according to a second embodiment of the present invention.

As shown in FIG. 8, the imaging optical system 51 and the projection optical system 61 are formed of cylinder-shaped gradient index lenses having outer diameters (lens diameters) that are approximately equal to each other. The imaging optical system 51 and the projection optical system 61 are integrally formed by combining a distal-end face of the gradient index lens that forms the imaging optical system 51 and a base-end face of the gradient index lens that forms the projection optical system 61. Although FIG. 8 shows the imaging optical system 51, which focuses illumination light entering from the emission end 13a of the optical fiber 13 once, the imaging optical system 51 may also be configured to focus the illumination light twice or more.

According to this embodiment, the imaging optical system 51 and the projection optical system 61 are each formed of a single member, thereby making it possible to facilitate assembly work in the manufacturing process.

Figure 9:
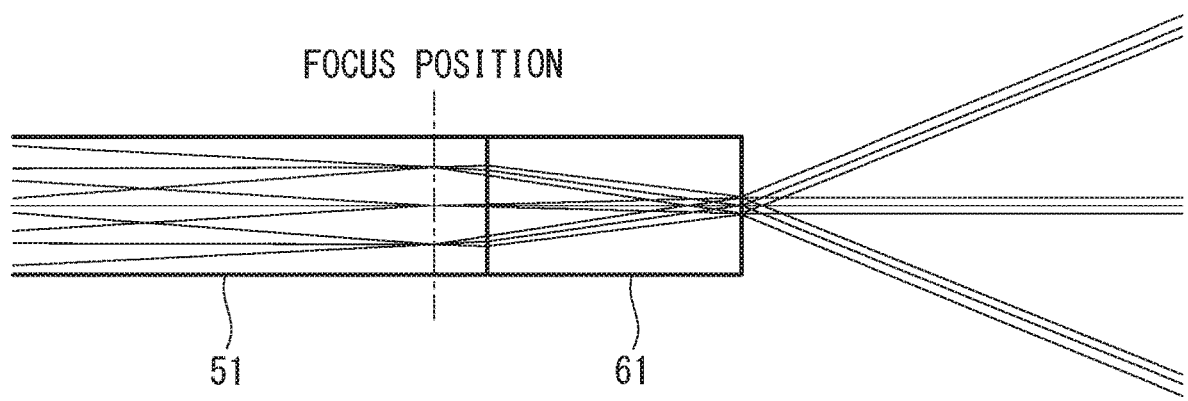
FIG. 9 is an enlarged view of a distal end section of the imaging optical system shown in FIG. 8.

In this embodiment, as shown in FIG. 9, it is preferred that the combined surfaces of the gradient index lenses be disposed at a position different from the focus position of illumination light focused by the imaging optical system 51.

Because the energy density is high at the focus position of illumination light, if the combined surfaces are disposed at a position identical to the focus position, there is a possibility that an adhesive agent is heated, thus changing the optical state at the combined surfaces. Furthermore, when the combined surfaces are disposed at a position that is optically conjugated with the focus position, an image of a scratch, dust, or the like on the combined surfaces is included in illumination light to be radiated on the subject S. According to this modification, it is possible to prevent the occurrence of such a disadvantage by disposing the combined surfaces at a position different from the focus position.

Figure 10:
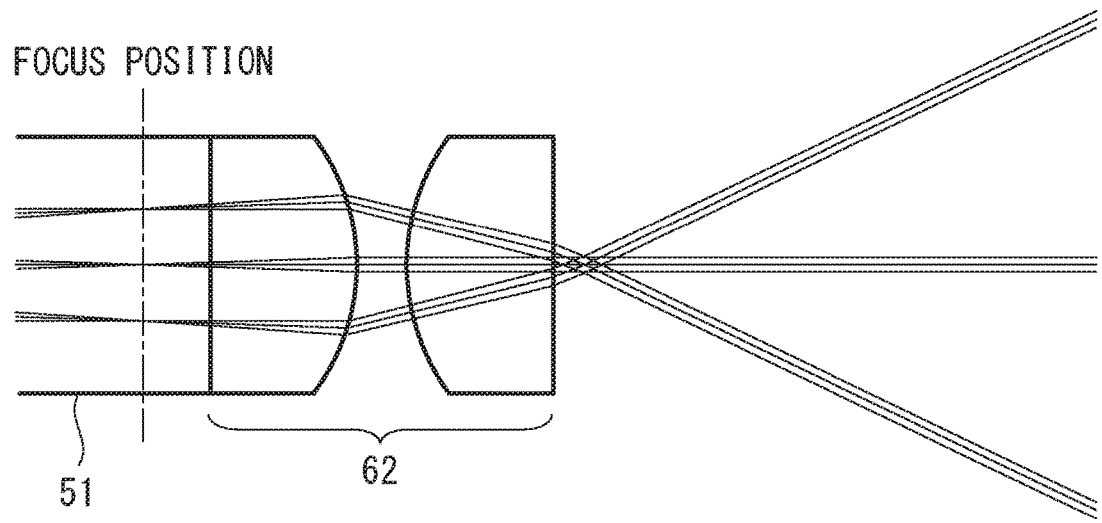
FIG. 10 is a view showing the configuration of a modification of the projection optical system shown in FIG. 8.

In this embodiment, it is also possible to adopt a projection optical system 62 that is constituted by a plurality of lenses, as shown in FIG. 10, instead of the gradient index lens.

If the imaging optical system 51, which needs to have a length corresponding to the length of the insertion portion 1, is constituted by a plurality of lenses, many lenses are required, thus making assembly difficult. On the other hand, the projection optical system 62 can be constituted by a small number of lenses. Therefore, in order to expand the angle of view, it is preferred that the gradient index lens of the projection optical system be changed to a plurality of lenses. The lenses that constitute the projection optical system 62 may be glass molded lenses or plastic molded lenses.

Next, an optical-scanning-type observation device according to a third embodiment of the present invention will be described with reference to FIGS. 11 to 13.

In this embodiment, configurations that are different from those in the first and second embodiments are mainly described, the same reference signs are assigned to configurations that are common to those in the first and second embodiments, and a description thereof will be omitted.

The optical-scanning-type observation device of this embodiment is provided with the light source 3, the optical scanner 4, an imaging optical system 52, the projection optical system 61, the light-receive 7, the image acquisition unit 8, and the controller 9 and is further provided with a correction optical system that corrects an incidence angle of illumination light entering the imaging optical system 52.

Figure 11:
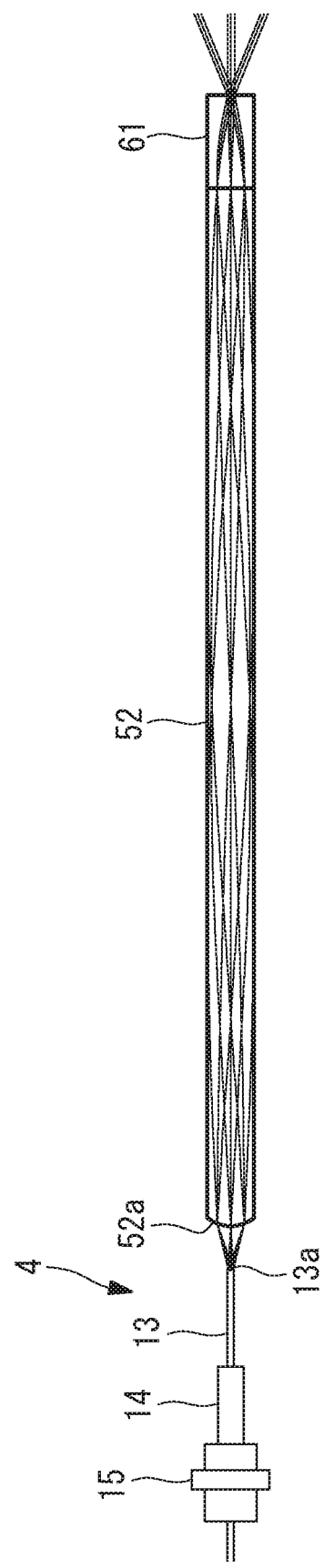
FIG. 11 is a view showing the configuration of an optical scanner, an imaging optical system, and a projection optical system in an optical-scanning-type observation device according to a third embodiment of the present invention.
Figure 12:
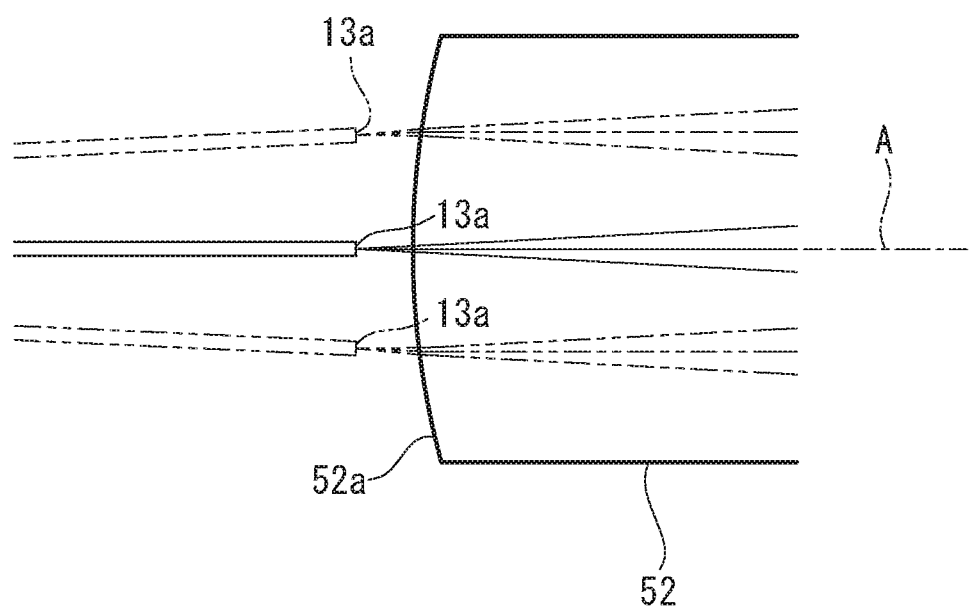
FIG. 12 is a partially enlarged view of the imaging optical system shown in FIG. 11.

As shown in FIG. 11, the imaging optical system 52 is formed of a cylinder-shaped gradient index lens. As shown in FIG. 12, a base-end face of the gradient index lens is a convex face 52a and is disposed so as to face the emission end 13a.

When the emission end 13a is vibrating, illumination light is emitted therefrom in diagonal directions with respect to an optical axis A of the imaging optical system 52 through bending of the distal end section of the optical fiber 13. The convex face 52a is designed in accordance with the inclination of the chief ray of illumination light with respect to the optical axis A of the imaging optical system 52, such that the chief ray of illumination light inclined with respect to the optical axis A of the imaging optical system 52 is brought close to parallel to the optical axis A of the imaging optical system 52. Accordingly, illumination light, of which the angle of the chief ray has been corrected at the convex face 52a so as to be parallel to the optical axis A of the imaging optical system 52, enters the imaging optical system 52. Specifically, the correction optical system is formed of the convex face 52a of the imaging optical system 52. Here, bringing illumination light close to parallel means that an incidence angle of the chief ray of illumination light is brought close to parallel, at a level where vignetting is not caused in the chief ray of illumination light in the projection optical system 61 and the imaging optical system 52.

The angle of view (illumination-light scanning zone) of an image acquired by the optical-scanning-type observation device can be expanded by increasing the amplitude of the emission end 13*a* of the optical fiber 13. However, because illumination light that can enter the imaging optical system 52 from the emission end 13*a* is limited to illumination light passing through a region prescribed by a numerical aperture (NA) at an incident side of the imaging optical system 52, if the amplitude of the emission end 13*a* is increased excessively, vignetting is caused by illumination light that does not enter the imaging optical system 52.

According to this embodiment, inclination of the chief ray of illumination light is corrected such that the chief ray of illumination light that enters the imaging optical system 52 becomes parallel to the optical axis A; thus, illumination light that is emitted from the emission end 13*a* at a position radially more displaced with respect to the optical axis A of the imaging optical system 52 can also be made to enter the imaging optical system 52 without causing vignetting. Therefore, there is an advantage in that an image having a wider angle can be acquired by increasing the amplitude of the emission end 13*a*.

Correction of inclination of the chief ray of illumination light is also important in terms of suppression of aberration and improvement of resolution. Specifically, as the chief ray comes closer to the rim of a lens, vignetting tends to be caused around the Gaussian distribution of laser light. If vignetting is caused around the Gaussian distribution while laser light passes through the lens, when the laser light is focused in a spot-like manner, the intensity distribution deviates from an ideal Gaussian distribution, and the size of the spot light is increased, thereby reducing the resolution. Thus, it is desirable that the chief ray be made parallel to the optical axis of the lens as much as possible.

According to this embodiment, by correcting inclination of the chief ray of illumination light, rays passing through the imaging optical system 52 are distributed close to the optical axis A of the imaging optical system 52, and rays passing through the circumferential edge of the imaging optical system 52, at which aberration tends to be caused, are reduced, thereby making it possible to suppress the occurrence of aberration. Furthermore, by suppressing aberration, the intensity distribution of spots of illumination light formed on the subject S is brought close to an ideal, and smaller spots can be realized on the subject S, thereby making it possible to improve the resolution.

Inclination of the chief ray of illumination light can be corrected merely through processing of one end face of the gradient index lens that forms the imaging optical system 52, thus making it unnecessary to add a lens. In this way, there is an advantage in that inclination of the chief ray of illumination light can be corrected with a simple configuration.

Figure 13:
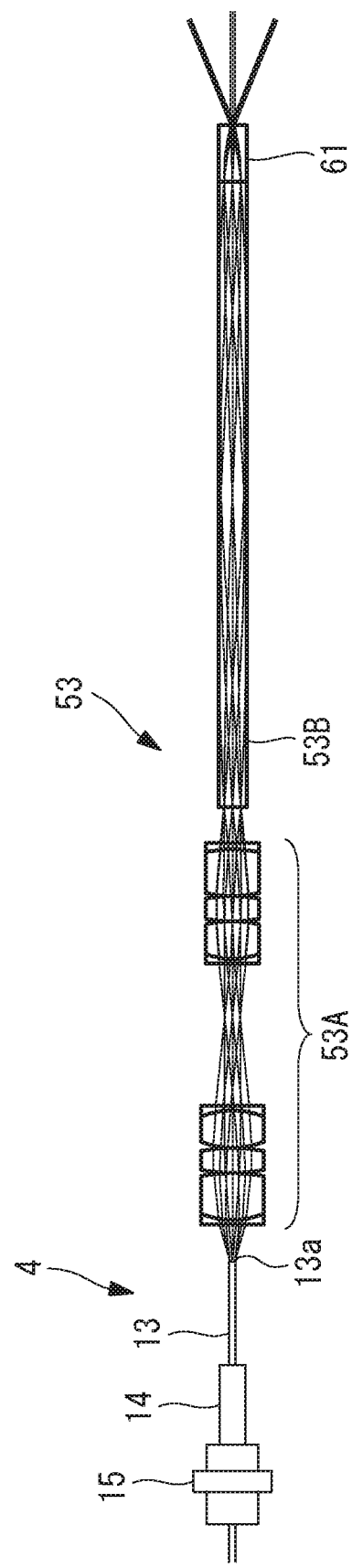
FIG. 13 is a view showing the configuration of a modification of the imaging optical system shown in FIG. 11.

In this embodiment, although the correction optical system is formed of the end face of the imaging optical system 52, instead of this, as shown in FIG. 13, the correction optical system may also be formed of at least one lens.

An imaging optical system 53 shown in FIG. 13 is provided with: a first imaging optical system 53A; and a second imaging optical system 53B that is disposed close to a distal end (emission side) of the first imaging optical system 53A and that is the same as the imaging optical system 51, which is shown in FIG. 8. It is preferred that the second imaging optical system 53B have approximately the same lens diameter as the projection optical system 61 and be formed integrally with the projection optical system 61. In this case, for example, the first imaging optical system 53A is included in the housing 2, and the second imaging optical system 53B is included in the insertion portion 1, thereby making it possible to reduce the diameter of the insertion portion 1. In this way, the imaging optical system and the projection optical system of the optical-scanning-type observation probe need not be provided in a single part, may be divided into a plurality of sections at an intermediate position of the optical axis, and may be provided in separate parts.

The first imaging optical system 53A is constituted by a plurality of lenses, corrects inclination of the chief ray of illumination light that has entered the first imaging optical system 53A from the emission end 13*a*, and emits illumination light that has the chief ray parallel to the optical axis, toward the second imaging optical system 53B. Specifically, the correction optical system is formed of the first imaging optical system 53A.

In this way, the imaging optical system 53 is constituted by two optical systems 53A and 53B, and the function as the correction optical system is assigned to the first imaging optical system 53A, which is located at a position close to the optical fiber 13, where design constraints are loose compared with the second imaging optical system 53B and the projection optical system 61, which are preferred to have small-diameter structures suitable for a rigid endoscope, thereby making it possible to facilitate design and manufacturing of the correction optical system.

Specifically, the correction optical system is designed such that an incidence angle is brought close to the optical axis A of the imaging optical system 52 at a level where vignetting is not caused in the chief ray of illumination light in the projection optical system 61 and the imaging optical system. In the optical system that is not provided with the correction optical system, shown in FIG. 8, for example, the inclination of the chief ray with respect to the optical axis A is 4.0 deg., the maximum amplitude is limited to 130 um, and the angle of view is limited to 58.2 deg. In contrast to this, in the optical system that is provided with the correction optical system, shown in FIG. 12, by correcting the inclination of the chief ray to 0.7 deg., the maximum amplitude can be increased to 160 um, and the angle of view can be widened to 76.2 deg. Furthermore, in the optical system that is provided with the correction optical system, shown in FIG. 13, by correcting the inclination of the chief ray to 0.03 deg., the maximum amplitude can be increased to 170 um, and the angle of view can be further widened to 77.9 deg.

In this way, by providing a correction optical system to bring the chief ray close to parallel to the optical axis A, the chief ray emitted from the fiber emission end at the time of the maximum amplitude of the optical fiber does not cause vignetting, thus making it possible to achieve a wide angle of view.

When the imaging optical system 53, which is constituted by the first and second imaging optical systems 53A and 53B, is adopted, it is preferred that a lens surface of the second imaging optical system 53B be disposed at a position different from the focus position of illumination light focused by the first imaging optical system 53A.

In this way, by disposing the lens surface of the second imaging optical system 53B at a position that is not optically conjugated with the focus position, it is possible to prevent an image of a scratch, dust, or the like on the lens surface from being included in illumination light.

Figure 14:
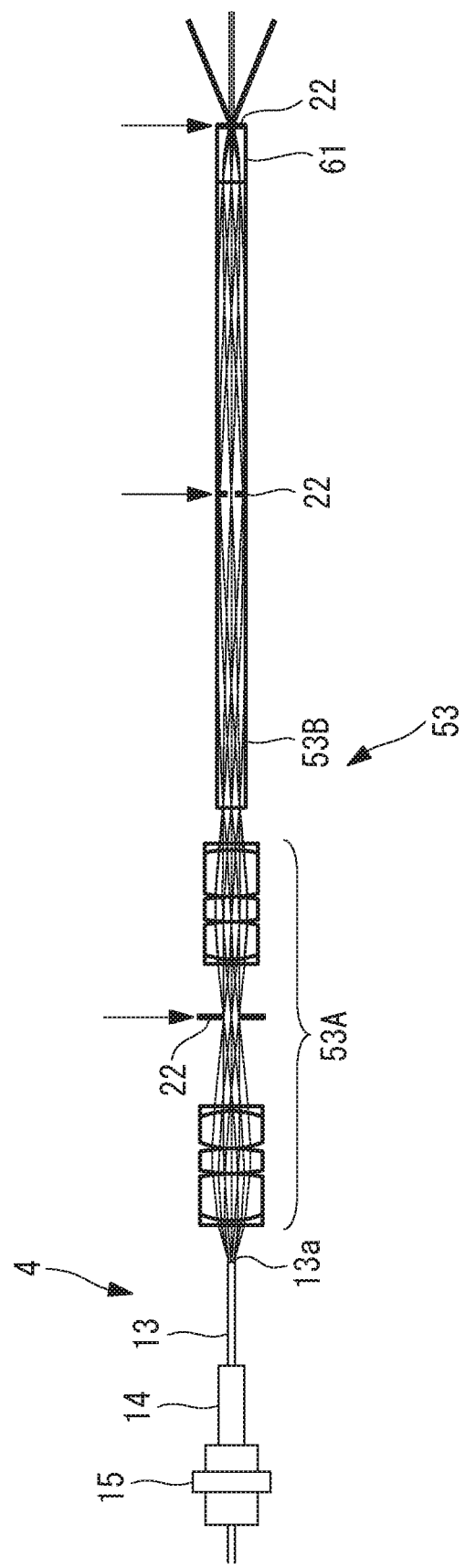
FIG. 14 is a view showing the configuration of an optical scanner, an imaging optical system, a projection optical system, and aperture stops in an optical-scanning-type observation device according to a fourth embodiment of the present invention.

Next, an optical-scanning-type observation device according to a fourth embodiment of the present invention will be described with reference to FIG. 14.

In this embodiment, configurations that are different from those in the first to third embodiments are mainly described, the same reference signs are assigned to configurations that are common to those in the first to third embodiments, and a description thereof will be omitted.

The optical-scanning-type observation device of this embodiment is provided with the light source 3, the optical scanner 4, the imaging optical system 53, the projection optical system 61, the light-receiver 7, the image acquisition unit 8, and the controller 9 and is further provided with an aperture stop 22 that limits the amount of illumination light that passes therethrough.

The aperture stop 22 has an aperture disposed on the optical axis of the optical systems 53 and 61 and allows illumination light to pass only through the aperture. The aperture stop 22 is disposed in the vicinity of at least one of pupil positions (arrow positions in FIG. 14) in the imaging optical system 53 and the projection optical system 61. The aperture stop 22 may be provided at just one place or at a plurality of places.

The aperture stop 22 can be provided in the imaging optical system 53B, which is formed of the gradient index lens, by cutting the gradient index lens at the position corresponding to the pupil position, by coating the peripheral edges of cut surfaces with a shading material in a ring-like manner, and by combining the cut surfaces.

The aperture stop 22 can be provided in the projection optical system 61 by coating the peripheral edge of the distal-end face thereof corresponding to the pupil position with a shading material in a ring-like manner.

In the imaging optical system 53, flares and ghosts may occur when illumination light is reflected at the side surfaces of the lenses that constitute the imaging optical system 53. According to this embodiment, it is possible to prevent such flares and ghosts by means of the aperture stop 22 and to improve the image quality.

The aperture stop 22 can also be applied to the above-described other imaging optical systems 5, 51, and 52 and the above-described other projection optical systems 6 and 62.

In the second, third, or fourth embodiment, in which a gradient index lens is used as the imaging optical system 51, 52, or 53, illumination light needs to be focused multiple times in the gradient index lens, which is long and narrow, in order to make the illumination light propagate from the emission end 13a of the optical fiber 13 to the projection optical system 61 or 62, which is located at the distal end of the insertion portion 1. Example specifications of such a gradient index lens (the diameter and the length of the gradient index lens, and the number of times illumination light is focused therein) will be shown below.

(Specification 1)
Diameter=0.25 mm
Length=62 mm
The number of times illumination light is focused=32
(Specification 2)
Diameter=0.35 mm
Length=62 mm
The number of times illumination light is focused=8
(Specification 3)
Diameter=0.70 mm
Total length=67 mm
The number of times illumination light is focused=3

In the first to fourth embodiments, it is also possible to further provide an optical system that corrects aberration caused in illumination light in the imaging optical system and the projection optical system.

In the case in which an imaging optical system that is constituted by first and second imaging optical systems, like the imaging optical system 53, is adopted, it is preferred that the first imaging optical system, which is located close to the optical fiber 13, be used to correct aberration, aberration of the first imaging optical system be designed so as to be inverted with respect to and so as to have the same size as aberration of the second imaging optical system and the projection optical system, and the aberration of the second imaging optical system and the projection optical system be offset by the aberration of the first imaging optical system. In this way, the function of correcting aberration is assigned to the first imaging optical system, which is located at a position close to the optical fiber 13, where design constraints are loose compared with the second imaging optical system and the projection optical system, which are preferred to have small-diameter structures suitable for a rigid endoscope, thereby making it possible to further facilitate design and manufacturing.

Note that examples of aberration that occur in the second imaging optical system and the projection optical system include axial chromatic aberration, chromatic aberration of magnification, curvature of field, spherical aberration, astigmatism, distortion, coma aberration, etc.

In the first to fourth embodiments, it is also possible to further include an adjustment mechanism that adjusts the relative positions of the emission end 13a of the optical fiber 13 and the imaging optical system 5, 51, 52, or 53, in a direction parallel to the optical axis and in a direction perpendicular to the optical axis.

By changing the relative positions of the emission end 13a of the optical fiber 13 and the imaging optical system 5, 51, 52, or 53 in a direction parallel to the optical axis, it is possible to move the focus position of illumination light in the direction parallel to the optical axis to perform alignment (focusing) of the final focus position with respect to the focal plane of the projection optical system 6, 61, or 62. Furthermore, by changing the relative positions of the emission end 13a of the optical fiber 13 and the imaging optical system 5, 51, 52, or 53 in a direction perpendicular to the optical axis, it is possible to move the focus position in the direction perpendicular to the optical axis to perform alignment (eccentricity adjustment) between the center of a spot of illumination light formed at the final focus position and the optical axis of the projection optical system 6, 61, or 62.

In this case, the adjustment mechanism is provided at a position close to the optical fiber 13, where design constraints are loose, thereby making it possible to further facilitate the focusing and the eccentricity adjustment.

In the case in which an imaging optical system that is constituted by first and second imaging optical systems, like the imaging optical system 53, is adopted, it is possible to design the first imaging optical system so as to secure a greater distance for relative-position adjustment, between the emission end 13a of the optical fiber 13 and the first imaging optical system, by using a high degree of freedom in design of the first imaging optical system. Accordingly, it is possible to further facilitate adjustment of the relative positions of the emission end 13a and the first imaging optical system. Furthermore, in the manufacturing process, assembly work of the optical fiber 13 and the first imaging optical system is facilitated.

In this modification, it is also possible to adopt an imaging optical system that has a projection magnification less than 1, such that the diameter of a spot of illumination light in the emission end 13a is reduced at the final focus position. By doing so, it is advantageous because it is possible to relax the precision of the relative positions of the emission end 13a and the imaging optical system, which is required in focus adjustment.

The amount of change in position, in the optical-axis direction, of the final focus position of illumination light caused by a change in the relative positions of the emission end 13a and the imaging optical system is proportional to the square of a projection magnification of the imaging optical system. Therefore, in the case in which an imaging optical system having a projection magnification less than 1 is used, the amount of deviation in position between the final focus position and the focal plane of the projection optical system is reduced compared with a case in which an imaging optical system whose projection magnification is equal magnification is used, as shown in FIG. 8, 11, or 14.

In the first to fourth embodiments, it is preferred that the controller 9 control the magnitude of a voltage to be supplied to the actuator 14 such that the maximum value of a half amplitude h (mm) of the emission end 13a of the optical fiber 13 satisfies the following expression (1):

$$h \leq \pi \times d \times D \times NA'/4\lambda \tag{1}$$

where, d is a mode field diameter (mm) of the optical fiber 13, λ is a wavelength (nm) of illumination light, D is an entrance pupil diameter (mm) of the imaging optical system, and NA' is a numerical aperture at the incident side of the imaging optical system.

The expression (1) prescribes an optical projection condition for illumination light emitted from the emission end 13a of the optical fiber 13 to be transmitted to the imaging optical system without being wasted. In the case in which the imaging optical system 53, which is constituted by the first and second imaging optical systems 53A and 53B, is adopted, D is an entrance pupil diameter of the second imaging optical system 53B, and NA' is a numerical aperture at the incident side of the second imaging optical system. By satisfying the expression (1), the optical performance of the optical scanner and the imaging optical system is maximized, thus making it possible to improve the image quality.

The expression (1) is derived as follows by taking an example case in which the imaging optical system 53, which is constituted by the first and second imaging optical systems 53A and 53B, is used.

NA at the emission end 13a of the optical fiber 13 and the projection magnification β of the first imaging optical system 53A are expressed as follows.

$$NA = \sin(2\lambda/\pi d) \approx 2\lambda/\pi d \tag{a}$$

$$\beta = NA/NA' = 2\lambda/\pi d NA' \tag{b}$$

On the other hand, a condition for illumination light emitted from the emission end 13a to be transmitted to the imaging optical system 53 without being wasted is expressed by the following expression.

$$2h \times \beta \leq D \tag{c}$$

The expression (1) is derived from the expressions (b) and (c).

It is also possible to provide, at the emission end 13a of the optical fiber 13, a lens surface for focusing illumination light emitted from the emission end 13a. The lens surface may be provided by forming a distal-end surface of the core of the optical fiber 13 into a spherical surface or may be provided by combining a gradient index lens with the emission end 13a, which is flat. By doing so, illumination light emitted from the emission end 13a is focused, and the illumination light enters the imaging optical system from the focus point. This is equivalent to reducing the mode field diameter d of the optical fiber 13.

In this case, it is preferred that the controller 9 control the magnitude of a voltage to be supplied to the actuator 14 such that the maximum value of the half amplitude h satisfies the following expression (1'). In the expression (1)', d' is a spot diameter (mm) of illumination light at the focus point.

$$h \leq \pi \times d' \times D \times NA'/4\lambda \tag{1'}$$

In the first to fourth embodiments, although reflected light having approximately the same wavelength as the wavelength of illumination light is detected, instead of this, it is also possible to detect signal light (for example, fluorescence excited by illumination light) that has a different wavelength from the wavelength of illumination light.

Because signal light is detected via a light path that is independent of a light path of illumination light, it is possible to arbitrarily select the wavelength of signal light independently of the wavelength of illumination light. Furthermore, unlike in a case in which a light path of illumination light and a light path of signal light are common, even when signal light having the same wavelength as the wavelength of illumination light is detected, the SN ratio of signal light to be detected is prevented from being reduced.

Note that the present invention is not limited to the above-described embodiments and can be appropriately modified without departing from the scope of the present invention.

For example, the optical scanner may also have the following configuration.

For example, as the optical scanner, it is also possible to use: a cylinder-shaped permanent magnet that is magnetically attached in the longitudinal direction and that has magnetic poles at both ends; and electromagnetic coils that are provided at positions opposed to the respective magnetic poles of the permanent magnet. An optical fiber is inserted into the permanent magnet so as to protrude from the permanent magnet, and the permanent magnet is fixed to an outer circumferential surface of the optical fiber. By supplying an electric current from the controller to the electromagnetic coils, the electromagnetic coils produce magnetic fields in the vicinities of the magnetic poles of the permanent magnet, thus vibrating the permanent magnet and vibrating the optical fiber.

As the optical scanner, it is also possible to use a galvanometer mirror that two-dimensionally scans illumination light.

Figure 15:
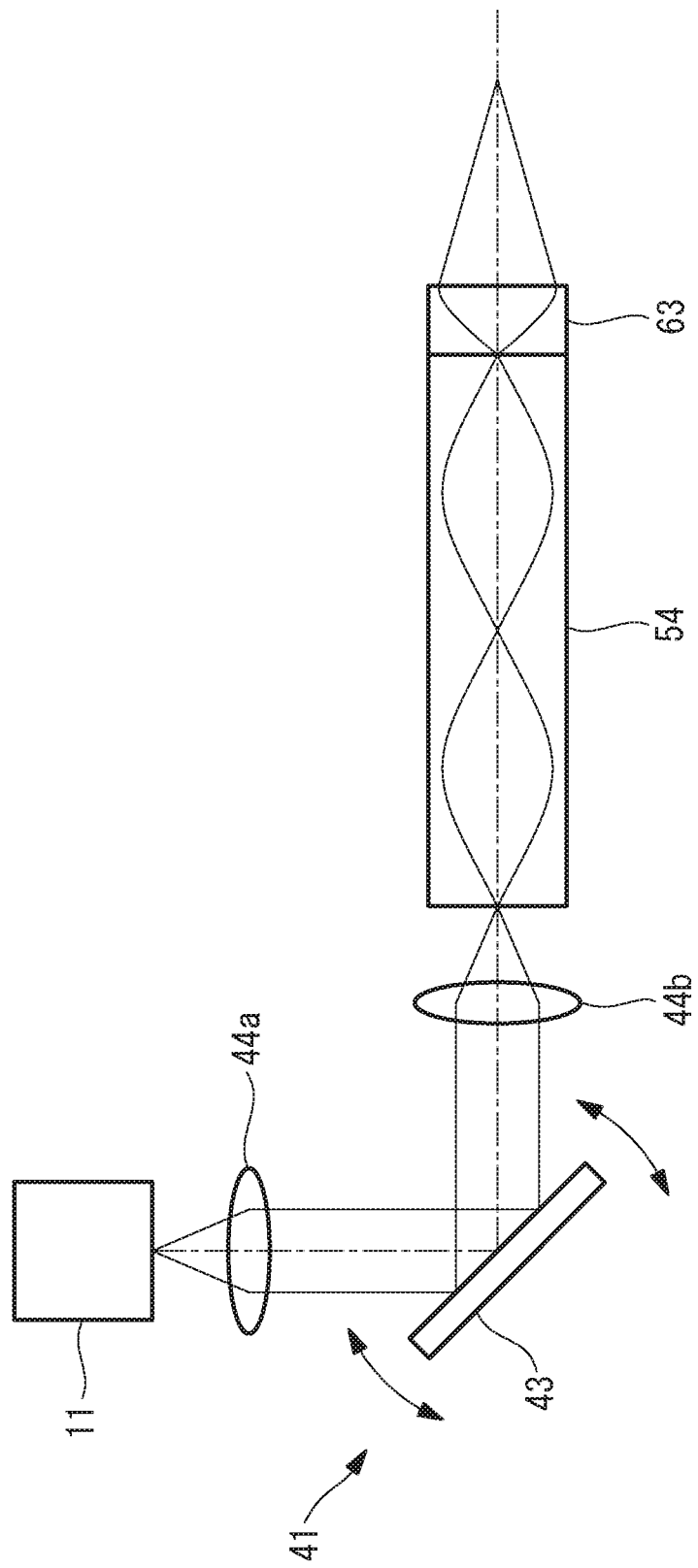
FIG. 15 is a view showing an example optical scanner using a galvanometer mirror.
Figure 16:
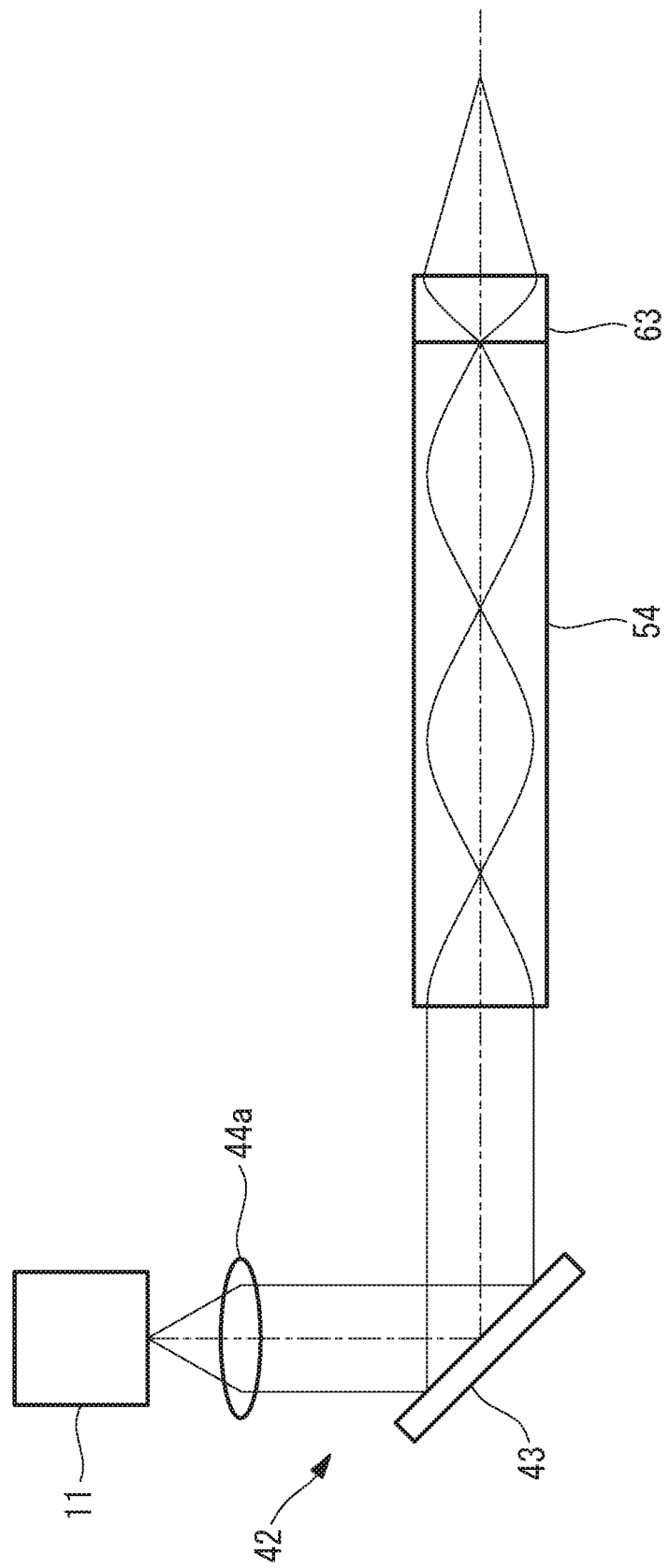
FIG. 16 is a view showing another example optical scanner using a galvanometer mirror.

FIGS. 15 and 16 respectively show example cases in which optical scanners 41 and 42 are each provided with a galvanometer mirror 43. It is possible to adopt, as an imaging optical system 54, any one of the above-described imaging optical systems 5, 51, 52, and 53, and to adopt, as a projection optical system 63, any one of the above-described projection optical systems 6, 61, and 62.

The optical scanner 41, which is shown in FIG. 15, is provided with: a collimator lens 44a that is disposed between a laser light source (light source) 11 and the galvanometer mirror 43; and a condenser lens 44b that is disposed between the galvanometer mirror 43 and the imaging optical system 54. Illumination light produced by the light source 11 is collimated by the collimator lens 44a and is incident on the galvanometer mirror 43. The illumination light reflected by the galvanometer mirror 43 is focused, by the condenser lens 44b, in the vicinity of an incident end of a gradient index lens that serves as the imaging optical system 54. Although illumination light is focused on a position deviated from the center of the imaging optical system 54 when the galvanometer mirror 43 is inclined, the condenser lens 44b is designed such that the chief ray of the illumination light when entering the imaging optical system 54 becomes parallel to the optical axis. For example, a front focus position of the condenser lens 44b is disposed in the vicinity of the center of the galvanometer mirror 43.

As shown in FIG. 16, it is also possible to remove the condenser lens 44b to cause illumination light reflected by the galvanometer mirror 43 to enter the imaging optical system 54 as parallel light, and to change the pitch of the gradient index lens. With this configuration, it is desirable that the galvanometer mirror 43 and the imaging optical system 54 be closer to each other in order to reduce vignetting of the illumination light.

With regard to the pitch of a gradient index lens, 0.5 pitch means the length of a lens in which an object image formed at one end of the lens is formed just once at the other end of the lens. Furthermore, 0.25 pitch means the length of a lens in which parallel light entering one end of the lens is focused just once at the other end of the lens. For example, in FIG. 15, because the gradient index lens 54 focuses illumination light twice, the pitch of the gradient index lens 54 is 1.0. Furthermore, in FIG. 16, because the gradient index lens 54 focuses parallel light three times, the pitch of the gradient index lens 54 is 1.25.

Although FIGS. 15 and 16 each show the single galvanometer mirror 43, which is capable of swinging about two axes intersecting each other, it is also possible to provide two galvanometer mirrors that are each capable of swinging about one axis.

With regard to guiding of illumination light from the light source 11 to the collimator lens 44a, it is also possible to directly collimate, by means of the collimator lens 44a, illumination light from a light-emitting part of the laser light source 11, or it is also possible to guide, by means of a single-mode fiber, illumination light produced by the laser light source 11 and to collimate, by means of the collimator lens 44a, the illumination light emitted from the emission end of the single-mode fiber.

When the galvanometer mirror 43 swings at a swing angle of ±α, it is preferred that the total swing angle 2α of the galvanometer mirror 43 satisfy the following expression (2):

$$\tan(2\alpha) \leq D \times NA'/w \quad (2),$$

where, D is an entrance pupil diameter of the imaging optical system 54 (gradient index lens), NA' is a numerical aperture at the incident side of the imaging optical system 54, and w is the diameter of a luminous flux of collimated illumination light incident on the galvanometer mirror 43.

In FIG. 15, in order to prevent the occurrence of flares and ghosts caused by reflecting illumination light at the side surface of the imaging optical system 54, the focusing numerical aperture of the lens 44b, w/(2×f), should be equal to or less than NA', as indicated by the following expression (d). f is the focal length of the lens 44b.

$$w/(2 \times f) \leq NA' \quad (d)$$

On the other hand, when the galvanometer mirror 43 is inclined at an angle α, because the angle of illumination light emitted from the galvanometer mirror 43 changes by 2α, the focus position of the illumination light focused by the condenser lens 44b is deviated from the optical axis of the imaging optical system 54 by f×tan(2α), in a direction perpendicular to the optical axis. Thus, a condition for preventing vignetting caused by illumination light in the imaging optical system 54 is shown in the following expression (e).

$$f \times \tan(2\alpha) \leq D/2 \quad (e)$$

The expression (2) is derived from the expressions (d) and (e).

As a result, the following aspect is read from the above described embodiment of the present invention.

According to a first aspect, the present invention provides an optical-scanning-type observation probe including: an imaging optical system that illumination light scanned by an optical scanner enters and that focuses the illumination light in the form of a spot, multiple times; a projection optical system that emits the illumination light coming from a focus position focused by the imaging optical system, toward a subject in the form of a spot; and a light-receiver that is provided independently of the imaging optical system and the projection optical system and that receives signal light produced in the subject through irradiation of the illumination light, via a light path different from that of the imaging optical system and the projection optical system.

According to the first aspect of the present invention, illumination light that has entered the imaging optical system is guided by the imaging optical system and the projection optical system and is radiated onto a subject by the projection optical system, and signal light from the subject, the signal light being produced through irradiation of the illumination light, is received by the light-receiver. At this time, because the illumination light enters the imaging optical system while being scanned by the optical scanner, the illumination light can be scanned on the subject. Furthermore, by providing the imaging optical system, which guides the illumination light emitted from the optical scanner to the projection optical system while focusing the illumination light multiple times, it is possible to form a configuration suitable for a rigid endoscope.

In this case, because signal light is received by the light-receiver, which is independent of the imaging optical system and the projection optical system for guiding illumination light, reflected light and scattered light of the illumination light that occur in the imaging optical system and the projection optical system are not mixed into signal light to be received. Accordingly, it is possible to observe signal light with a high signal-to-noise ratio.

The above-described first aspect may further include a correction optical system that corrects inclination of a chief ray of the illumination light scanned by the optical scanner and entering the imaging optical system, with respect to the optical axis of the imaging optical system, so as to bring the chief ray close to parallel to the optical axis.

By doing so, when the scan width of illumination light scanned by the optical scanner is increased in order to expand the illumination-light scanning zone on the subject, it is possible to reduce vignetting caused by illumination light that does not enter the imaging optical system. Furthermore, in the imaging optical system, rays of illumination light are distributed close to the optical axis, where the occurrence of aberration is less, thereby reducing aberration caused in the illumination light; therefore, the intensity distribution of spots of illumination light on the subject can be brought close to an ideal. Accordingly, smaller spots can be realized, thus making it possible to improve the resolution.

In the above-described first aspect, the imaging optical system may be provided with a gradient index lens whose end face, from which the illumination light scanned by the optical scanner enters, is a convex face; and the correction optical system may be formed of the convex face of the gradient index lens.

By doing so, due to the positive refractive power of the convex face, it is possible to correct inclination of the chief ray of illumination light entering the gradient index lens. Furthermore, without increasing the number of members, such as lenses, the correction optical system can be added merely through processing of one of end faces of the gradient index lens.

In the above-described first aspect, the imaging optical system may be constituted by: a first imaging optical system that the illumination light scanned by the optical scanner enters, that corrects inclination of the chief ray of the illumination light so as to bring the chief ray close to parallel to the optical axis, and that emits the illumination light for which inclination of the chief ray has been corrected; and a second imaging optical system that is disposed on an emission side of the first imaging optical system; and the correction optical system may be formed of the first imaging optical system.

In this way, the imaging optical system is constituted by the first imaging optical system and the second imaging optical system, thereby making it possible to cause the second imaging optical system, which is located on the emission side, and the projection optical system to have a thin structure suitable for a rigid endoscope and making it possible to precisely correct inclination of the chief ray of illumination light by means of the first imaging optical system, which is located at a position close to the optical scanner, where design constraints are loose.

In the above-described first aspect, the imaging optical system may be constituted by a first imaging optical system and a second imaging optical system that is disposed on an emission side of the first imaging optical system; and the first imaging optical system may correct aberration that occurs in at least one of the projection optical system and the second imaging optical system.

In this way, the imaging optical system is constituted by the first imaging optical system and the second imaging optical system, thereby making it possible to cause the second imaging optical system, which is located on the emission side, and the projection optical system to have a thin structure suitable for a rigid endoscope and making it possible to precisely correct aberration by means of the first imaging optical system, which is located at a position close to the optical scanner, where design constraints are loose.

In the above-described first aspect, the imaging optical system may be constituted by a first imaging optical system and a second imaging optical system that is disposed on an emission side of the first imaging optical system; and the second imaging optical system may have a lens diameter approximately equivalent to a lens diameter of the projection optical system and may be integrated with the projection optical system.

In this way, the second imaging optical system and the projection optical system are each formed of a single member, thereby making it possible to facilitate assembly work in the manufacturing process.

The above-described first aspect may further include an aperture stop that is disposed in the vicinity of a pupil position of one of the imaging optical system and the projection optical system.

By doing so, the occurrence of optical noise, such as flares and ghosts, can be prevented by the aperture stop.

In the above-described first aspect, at least an emission-side part of the imaging optical system and the projection optical system may be each formed of a gradient index lens; and an emission-side end face of the gradient index lens that forms the imaging optical system and an incident-side end face of the gradient index lens that forms the projection optical system may be combined with each other.

By doing so, it is possible to facilitate assembly work of the imaging optical system and the projection optical system.

In the above-described first aspect, the combined faces of the gradient index lenses may be disposed at a position different from a focus position of the illumination light focused by the imaging optical system.

The energy density is high at a focused position of illumination light. By disposing the combined surfaces at a position different from such a focused position, it is possible to prevent a change in the optical state of the combined surfaces. Furthermore, because the combined surfaces are disposed at a position that is not optically conjugated with the focused position, it is possible to prevent an image of a scratch, dust, or the like on the combined surfaces from being included in illumination light to be radiated onto the subject.

In the above-described first aspect, the imaging optical system may be constituted by a first imaging optical system and a second imaging optical system that is disposed on an emission side of the first imaging optical system; and a lens surface of the second imaging optical system may be disposed at a position different from a focus position of the illumination light focused by the first imaging optical system.

By doing so, because the lens surface of the second imaging optical system is disposed at a position that is not optically conjugated with the focus position of illumination light, it is possible to prevent an image of a scratch, dust, or the like on the lens surface from being included in illumination light to be radiated onto the subject.

According to a second aspect, the present invention provides an optical-scanning-type observation device including: a light source that produces illumination light; an optical scanner that scans the illumination light emitted from the light source; and any one of the above-described optical-scanning-type observation probes.

In the above-described second aspect, the optical scanner may be provided with an optical fiber that guides the illumination light emitted from the light source and that emits the illumination light from a distal end thereof, and may vibrate the optical fiber in radial directions of the optical fiber so as to satisfy the following expression (1):
$h \leq \pi \times d \times D \times NA'/4\lambda$ (1),
where h is a half amplitude of a distal end of the optical fiber; d is a mode field diameter of the optical fiber; D is an entrance pupil diameter of the imaging optical system; NA' is a numerical aperture on an incident side of the imaging optical system; and $\lambda$ is a wavelength of the illumination light.

By doing so, it is possible to prevent flares and ghosts caused when illumination light is reflected at the side surface of a lens that constitutes the imaging optical system.

In the above-described second aspect, the optical scanner may be provided with a galvanometer mirror that scans the illumination light emitted from the light source, and may swing the galvanometer mirror so as to satisfy the following expression (2): $\tan(2\alpha) \leq D \times NA'/w$ (2), where α is half of the total swing angle of the galvanometer mirror; w is a luminous flux diameter of the illumination light incident on the galvanometer mirror; NA' is a numerical aperture on an incident side of the imaging optical system; and D is an entrance pupil diameter of the imaging optical system.

By doing so, it is possible to prevent flares and ghosts caused when illumination light is reflected at the side surface of a lens that constitutes the imaging optical system.

In the above-described second aspect, the optical scanner may have an emission end from which the illumination light is emitted toward the imaging optical system; and the optical-scanning-type observation device may further include an adjustment mechanism that adjusts relative positions of the emission end of the optical scanner and the imaging optical system, in a direction parallel to the optical axis of the imaging optical system and in a direction perpendicular to the optical axis thereof.

When the relative positions of the emission end of the optical scanner and the imaging optical system are changed, the focus position of illumination light in the imaging optical system is changed. Therefore, it is possible to perform focus adjustment through adjustment of the relative positions of the emission end of the optical scanner and the imaging optical system in the direction along the optical axis, and to perform eccentricity adjustment through adjustment of the relative positions of the emission end of the optical scanner and the imaging optical system in a direction perpendicular to the optical axis. Furthermore, by providing the adjustment mechanism at a position close to the optical scanner, where design constraints are loose, it is possible to secure a large adjustment range used by the adjustment mechanism and to correct, by means of the adjustment mechanism, a deviation of the focus position caused by an error in assembly of the imaging optical system and the projection optical system. Specifically, it is possible to relax the assembly precision required for the imaging optical system and the projection optical system.

REFERENCE SIGNS LIST 100, 101, 102 optical-scanning-type observation device
1 insertion portion (optical-scanning-type observation probe)
2 housing
3 light source
4 optical scanner
5, 51, 52, 53, 54 imaging optical system
53A first imaging optical system
53B second imaging optical system
6, 61, 62, 63 projection optical system
7 light-receiver
8 image acquisition unit
9 controller
10 display
11R, 11G, 11B, 11 laser light source (light source)
12 light coupling unit
13 optical fiber
13a emission end
14 actuator
15 fixing part
16 inner cylinder
17 outer cylinder
18 light detector
19 A/D converter
20 image formation unit
22 aperture stop

The invention claimed is:

1. An optical-scanning-type observation probe comprising:
   an imaging optical system that illumination light scanned by an optical scanner enters and that is configured to focus the illumination light in the form of a spot, multiple times;
   a projection optical system that is configured to emit the illumination light coming from a focus position focused by the imaging optical system, toward a subject in the form of a spot; and
   a light-receiver provided independently of the imaging optical system and the projection optical system,
   wherein the light-receiver is configured to receive signal light produced in the subject through irradiation of the illumination light, via a light path different from that of the imaging optical system and the projection optical system.

2. An optical-scanning-type observation probe according to claim 1, further comprising a correction optical system that is configured to correct inclination of a chief ray of the illumination light scanned by the optical scanner and entering the imaging optical system, with respect to the optical axis of the imaging optical system, so as to bring the chief ray close to parallel to the optical axis.

3. An optical-scanning-type observation probe according to claim 2,
   wherein the imaging optical system is provided with a gradient index lens whose end face, from which the illumination light scanned by the optical scanner enters, is a convex face; and
   the correction optical system is formed of the convex face of the gradient index lens.

4. An optical-scanning-type observation probe according to claim 2,
   wherein the imaging optical system is constituted by:
      a first imaging optical system that the illumination light scanned by the optical scanner enters, that corrects inclination of the chief ray of the illumination light so as to bring the chief ray close to parallel to the optical axis, and that emits the illumination light for which inclination of the chief ray has been corrected; and
      a second imaging optical system that is disposed on an emission side of the first imaging optical system; and
   the correction optical system is formed of the first imaging optical system.

5. An optical-scanning-type observation probe according to claim 1,
   wherein the imaging optical system is constituted by a first imaging optical system and a second imaging optical system that is disposed on an emission side of the first imaging optical system; and
   the first imaging optical system corrects aberration that occurs in at least one of the projection optical system and the second imaging optical system.

6. An optical-scanning-type observation probe according to claim 1,
   wherein the imaging optical system is constituted by a first imaging optical system and a second imaging optical system that is disposed on an emission side of the first imaging optical system; and
   the second imaging optical system has a lens diameter approximately equivalent to a lens diameter of the projection optical system and is integrated with the projection optical system.

7. An optical-scanning-type observation probe according to claim 1, further comprising an aperture stop that is disposed in the vicinity of a pupil position of one of the imaging optical system and the projection optical system.

8. An optical-scanning-type observation probe according to claim 1,
wherein at least an emission-side part of the imaging optical system and the projection optical system are each formed of a gradient index lens; and
an emission-side end face of the gradient index lens that forms the imaging optical system and an incident-side end face of the gradient index lens that forms the projection optical system are combined with each other.

9. An optical-scanning-type observation probe according to claim 8, wherein the combined faces of the gradient index lenses are disposed at a position different from a focus position of the illumination light focused by the imaging optical system.

10. An optical-scanning-type observation probe according to claim 1,
wherein the imaging optical system is constituted by a first imaging optical system and a second imaging optical system that is disposed on an emission side of the first imaging optical system; and
a lens surface of the second imaging optical system is disposed at a position different from a focus position of the illumination light focused by the first imaging optical system.

11. An optical-scanning-type observation device comprising:
a light source that is configured to produce illumination light;
an optical scanner that is configured to scan the illumination light emitted from the light source; and
an optical-scanning-type observation probe according to claim 1.

12. An optical-scanning-type observation device according to claim 11, wherein the optical scanner is provided with an optical fiber that is configured to guide the illumination light emitted from the light source and that emits the illumination light from a distal end thereof, and vibrates the optical fiber in radial directions of the optical fiber so as to satisfy the following expression (1):

$$h \leq \pi \times d \times D \times NA'/4\lambda \quad (1),$$

where,
h is a half amplitude of a distal end of the optical fiber;
d is a mode field diameter of the optical fiber;
D is an entrance pupil diameter of the imaging optical system;
NA' is a numerical aperture on an incident side of the imaging optical system; and
$\lambda$ is a wavelength of the illumination light.

13. An optical-scanning-type observation device according to claim 11, wherein the optical scanner is provided with a galvanometer mirror that is configured to scan the illumination light emitted from the light source, and swings the galvanometer mirror so as to satisfy the following expression (2):

$$\tan(2\alpha) \leq D \times NA'/w \quad (2),$$

where,
$\alpha$ is half of the total swing angle of the galvanometer mirror;
w is a luminous flux diameter of the illumination light incident on the galvanometer mirror;
NA' is a numerical aperture on an incident side of the imaging optical system; and
D is an entrance pupil diameter of the imaging optical system.

14. An optical-scanning-type observation device according to claim 11,
wherein the optical scanner has an emission end from which the illumination light is emitted toward the imaging optical system; and
the optical-scanning-type observation device further comprises an adjustment mechanism that is configured to adjust relative positions of the emission end of the optical scanner and the imaging optical system, in a direction parallel to the optical axis of the imaging optical system and in a direction perpendicular to the optical axis thereof.

* * * * *